United States Patent [19]

Geelhaar et al.

[11] Patent Number: 5,064,569

[45] Date of Patent: Nov. 12, 1991

[54] OPTICALLY ACTIVE COMPOUNDS

[75] Inventors: Thomas Geelhaar, Mainz; Andreas Wächtler, Griesheim, both of Fed. Rep. of Germany; Bernhard Scheuble, Yokohama, Japan

[73] Assignee: Merck Patent Gesellschaft Mit Beschränkter Haftung, Darmstadt, Fed. Rep. of Germany

[21] Appl. No.: 445,104

[22] Filed: Dec. 7, 1989

Related U.S. Application Data

[63] Continuation of Ser. No. 116,944, filed as PCT/DE87/00035 Jan. 31, 1987, abandoned.

[30] Foreign Application Priority Data

Feb. 17, 1986 [DE] Fed. Rep. of Germany ....... 3604905
Sep. 10, 1986 [DE] Fed. Rep. of Germany ....... 3630771

[51] Int. Cl.$^5$ ............... C09K 19/12; C09K 19/52; C07C 41/00; C07C 69/76
[52] U.S. Cl. ............... 252/299.65; 252/299.01; 252/299.6; 252/299.64; 252/299.66; 252/299.67; 560/76; 560/138; 560/141; 568/643
[58] Field of Search ........... 252/299.01, 299.6, 299.64, 252/299.65, 299.66, 299.67; 560/76, 138, 141; 568/643

[56] References Cited

U.S. PATENT DOCUMENTS

| | | | |
|---|---|---|---|
| Re. 31,715 | 10/1984 | Coates et al. | 252/299.65 |
| 4,576,732 | 3/1986 | Isogai et al. | 252/299.65 |
| 4,589,996 | 5/1986 | Inoue et al. | 252/299.65 |
| 4,592,858 | 6/1986 | Higuchi et al. | 252/299.66 |
| 4,596,667 | 6/1986 | Inukai et al. | 252/299.65 |
| 4,613,209 | 9/1986 | Goodby et al. | 350/350.5 |
| 4,613,609 | 9/1986 | Inoue et al. | 252/299.66 |
| 4,637,897 | 1/1987 | Kelly et al. | 252/299.63 |
| 4,650,600 | 3/1987 | Heppke et al. | 252/299.01 |
| 4,688,427 | 5/1987 | Saito et al. | 252/299.66 |
| 4,695,651 | 9/1987 | Higuchi et al. | 252/299.66 |
| 4,728,458 | 3/1988 | Higuchi et al. | 252/299.65 |
| 4,732,699 | 3/1988 | Higuchi et al. | 252/299.66 |
| 4,744,918 | 5/1988 | Heppke et al. | 252/299.61 |
| 4,753,752 | 6/1988 | Raynes et al. | 252/299.65 |
| 4,754,051 | 6/1988 | Sasaki et al. | 252/299.64 |
| 4,959,173 | 9/1990 | Shibata et al. | 252/299.65 |
| 4,966,726 | 10/1990 | Scherowsky et al. | 252/299.6 |
| 4,988,458 | 1/1991 | Heppke et al. | 252/299.65 |
| 4,988,459 | 1/1991 | Scherowsky et al. | 252/299.61 |
| 4,997,591 | 3/1991 | Heppke et al. | 252/299.61 |

FOREIGN PATENT DOCUMENTS

| | | | |
|---|---|---|---|
| 164814 | 12/1985 | European Pat. Off. | 252/299.65 |
| 225195 | 6/1987 | European Pat. Off. | 252/299.61 |
| 3515373 | 11/1986 | Fed. Rep. of Germany | 252/299.61 |
| 3515374 | 11/1986 | Fed. Rep. of Germany | 252/299.61 |
| 240385 | 10/1986 | German Democratic Rep. | 252/299.61 |
| 240386 | 10/1986 | German Democratic Rep. | 252/299.61 |
| 58-46040 | 3/1983 | Japan | 252/299.66 |
| 62-181238 | 8/1987 | Japan | 252/299.65 |

*Primary Examiner*—John S. Maples
*Assistant Examiner*—Richard Treanor
*Attorney, Agent, or Firm*—Millen, White & Zelano

[57] ABSTRACT

Optically active compounds of the formula I can be used as components of chiral titled smectic liquid crystal phases:

$$R^1-C^*HX-Q-A^4-Z^1-A^2-(Z^2-A^3)_n-X'-Q'-C^*HY'-R^5 \quad (I)$$

wherein
$R^1-C^*HX-Q-$ and $-X'-Q'-C^*HY-R^5$ are identical optically active radicals selected from the group $-O-C^*HCH_3-COO-n-$alkyl, $-O-C^*HCH_3-CH_2-O-n-$alkyl, $-OCO-C^*HCl-CHCH_3-CH_3$, $-OCO-C^*HCl-C^*HCH_3-C_2H_5$, $-OCO-C^*HCl-CH_2-CHCH_3-CH_3$, $-OCO-C^*HCl-C(CH_3)_3$, $-COO-C^*HCH_3-COO-n-$alkyl, $-O-CO-C^*HCH_3-o-n-$alkyl, $-OCH_2-C^*HCH_3-O-n-$alkyl, $-COO-C^*HCH_3CH_2-O-n-$allyl, $-OC^*HCH_3-CH_2-COO-n-$alkyl, $-COO-C^*HCH_3-CH_2-COO-n-$alkyl, $-OCH_2-C^*HCH_3-COO-n-$alkyl or $-COO-CH_2-C^*HCH_3-COO-n-$alkyl, alkyl is of 1—12 c atoms, and $-A^4-Z^1-A^2-(Z^2-A^3)_n-$ is a group of the following formulae or a mirror image thereof:

(F)$_p$   (F)$_q$

1

2

(p = 1, 2, 3, or 4;
q = 0, 1, 2, 3 or 4)

3

(F)$_p$   (F)$_q$

4

(Abstract continued on next page.)

-continued
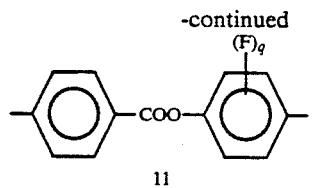
11
-continued
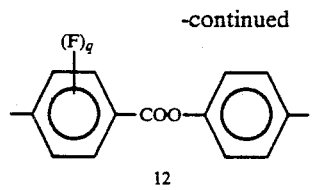
12
5 Claims, No Drawings

OPTICALLY ACTIVE COMPOUNDS

This application is a continuation of application Ser. No. 07/116,944, filed as PCT/DE87/00035 Jan. 31, 1987 now abandoned.

The invention relates to optically active compounds of the formula I

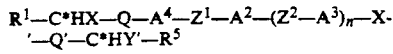

$$R^1\text{—C*HX—Q—A}^4\text{—Z}^1\text{—A}^2\text{—(Z}^2\text{—A}^3)_n\text{—X'—Q'—C*HY'—R}^5$$

wherein
- $R^1$ is an alkyl or perfluoroalkyl group with in each case 1-12 C atoms, it also being possible for one or two non-adjacent $CH_2$— or $CF_2$— groups to be replaced by 0 atoms and/or —CO— groups and/or —CO—O— groups and/or —CH=CH— groups and/or —CHhalogen— and/or —CHCN— groups and/or —O—CO—CHhalogen— and/or —O—CO—CHCN— groups,
- $R^5$ is an alkyl group with 1 to 15 C atoms which differs from Y', it also being possible for one or two non-adjacent $CH_2$— groups to be replaced by —O—, —CO—, —O—CO—, —CO—O— and/or —CH=CH—,
- $A^2$, $A^3$ are each 1,4-phenylene which is unsubstituted and $A^4$ or substituted by one or two F and/or Cl atoms and/or $CH_3$— groups and/or CN— groups, it also being possible for one or two CH— groups to be replaced by N, or 1,4-cyclohexylene, it also being possible for one or two non-adjacent $CH_2$— groups to be replaced by 0 atoms and/or S atoms, or piperidine-1,4-diyl, 1,4-bicyclo-(2,2,2)-octylene, naphthalene-2,6-diyl, decahydronaphthalene-2,6-diyl or 1,2,3, 4-tetrahydronaphthalene-2,6-diyl groups,
- $Z^1$ and $Z^2$ are each —CO—O—, —O—CO—, —$CH_2CH_2$—, —$OCH_2$—, —$CH_2O$—, —C≡C— or a single bond,
- X is halogen, CN or $CH_3$,
- n is 0 or 1,
- Q is alkylene with 1 to 4 C atoms, it also being possible for one $CH_2$— group to be replaced by —O—, —CO—, —O—CO—, —CO—O—, —CH=CH—COO—, —CH=CH—, -CHhalogen and/or —CHCN—, or a single bond,
- X' is —CO—O—, —O—CO—, —O—CO—O—, —CO—, —O—, —S—, —CH=CH—, —CH=CH—COO— or a single bond,
- Q' is alkylene with 1 to 5 C atoms, it also being possible for a $CH_2$— group which is not linked to X' to be replaced by —O—, —CO—, —O—CO, —CO—O— or —CH=CH—, or a single bond, and
- Y' is CN, halogen, methyl or methoxy, with the proviso that $R^1$ and/or $R^5$ is a branched alkyl group with 3 to 12 C atoms if —C*HX—Q— is —C*Hhalogen—CO—O— and/or —X'—Q'—C*HY'— is —O—CO—C*Hhalogen.

Like similar compounds described in German Offenlegungsschrift 3,515,373, the compounds of the formula I can be used as components of chiral tilted smectic liquid crystal phases.

Chiral tilted smectic liquid crystal phases with ferroelectric properties can be prepared by adding a suitable chiral doping substance to base mixtures with one or more tilted smectic phases (L. A. Beresnev et al., Mol. Cryst. Liq. Cryst. 89, 327 (1982); and H. R. Brand et al., J. Physique 44, (lett.), L-771 (1983)). Such phases can be used as dielectrics for rapid-switching displays based on the principle, described by Clark and Lagerwall, of SSFLC technology (N. A. Clark and S. T. Lagerwall, Appl. Phys. Lett. 36, 899 (1980); and U.S. Pat. No. 4,367,924), on the basis of the ferroelectric properties of the chiral tilted phase. The elongated molecules are aligned in layers in this phase, the molecules having an angle of tilt to the layer perpendicular. On progressing from layer to layer, the direction of tilt changes by a small angle in respect of an axis vertical to the layers, so that a helix structure is formed. In displays based on the principle of SSFLC technology, the smectic layers are arranged perpendicular to the plates of the cell. The helical arrangement of the tilt directions of the molecule is suppressed by a very low separation of the plates (about 1-2 μm). The longitudinal axes of the molecules are thereby forced to arrange themselves in a plane parallel to the plates of the cell, which means that two preferential tilt orientations are formed. By applying a suitable electrical alternating field, the liquid crystal phase, which has spontaneous polarization, can be switched back and forth between these two states. This switching operation is considerably faster than in conventional twisted cells (TN-LCD's) based on nematic liquid crystals.

A great disadvantage for many applications of the materials currently available with chiral tilted smectic phases (such as, for example, Sc*) is their relatively high optical anisotropy, not adequately short switching times caused by relatively high viscosity values and the fact that the dielectric anisotropy has values greater than zero or, if they are negative, values which differ only slightly from zero. Negative values of the dielectric anisotropy are necessary if the required planar orientation is effected by overlapping of the control field with an AC holding field of low amplitude (J. M. Geary, SID conference, Orlando/Florida, April/May 1985, paper 8.3).

It has now been found that the use of compounds of the formula I as components of chiral tilted smectic mixtures can substantially reduce the disadvantages mentioned. The compounds of the formula I are therefore outstandingly suitable as components of chiral tilted smectic liquid crystal phases. In particular, chiral tilted smectic liquid crystal phases of particularly high chemical stability and with advantageous ferroelectric phase ranges, in particular with wide Sc* phase ranges, negative or positive dielectric anisotropy, low optical anisotropy, a favourable pitch height and, for such phases, high values for spontaneous polarization and very short switching times can be prepared with the aid of these compounds. P is the spontaneous polarization in $nC/cm^2$.

By providing the compounds of the formula I, the range of liquid crystal substances which are suitable, from various technological viewpoints, for the preparation of ferroelectric mixtures is also considerably extended in a quite general way.

The compounds of the formula I have a wide range of application. Depending on the choice of the substituents, these compounds can be used as base materials from which liquid crystal phases are predominantly composed; however, it is also possible for compounds of the formula I to be added to liquid crystal base materials from other classes of compound, for example in order to vary the dielectric and/or optical anisotropy and/or the spontaneous polarization and/or the phase range and/or the angle of tilt and/or the pitch and/or the switching times of such a phase. The compounds of the formula I are furthermore suitable as intermediates for the preparation of other substances which can be used as constituents of liquid crystal phases.

The compounds of the formula I are colourless in the pure state and have low values for their optical anisotropy. The compounds of the formula I in some cases exhibit liquid crystal mesophases in a temperature range which is advantageously placed for electrooptical use, but isotropic or monotropic liquid crystal compounds of the formula I can also advantageously be used as components of chirally tilted smectic phases. They are very stable towards chemicals, heat and light.

The invention thus relates to the optically active compounds of the formula I and the use of the compounds of the formula I as components of liquid crystal phases.

The invention also relates to chiral tilted smectic liquid crystal phases with a content of at least one optically active compound of the formula I.

The invention furthermore relates to such phases with a content of at least one compound of the formula I and liquid crystal display elements, in particular electrooptical display elements, which contain such phases.

For simplicity, in the following text Ph is a 1,4-phenylene group, it also being possible for one or two CH— groups to be replaced by N, Cy is a 1,4-cyclohexylene group, it also being possible for one or two non-adjacent $CH_2$— groups to be replaced by 0 atoms, and Bi is a bicyclo(2,2,2)octylene group.

Above and below, $R^1$, $R^5$, n, $A^2$, $A^3$, $A^4$, Q, X, X', Q', Y', $Z^1$ and $Z^2$ have the meaning given, unless expressly indicated otherwise.

The compounds of the formula I accordingly include, in particular, compounds of the part formulae Ia and Ib (with two rings)

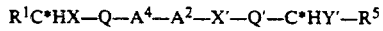    Ia

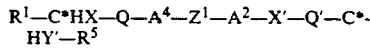    Ib and Ic to If (with three rings):

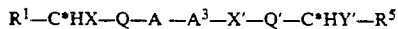    Ic

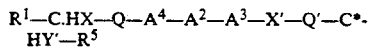    Id

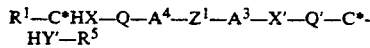    Ie

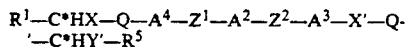    If

Amongst these, those of the formulae Ia, Ib, Ic, Id and Ie are particularly preferred.

The preferred compounds of the formula Ia include those of the part formulae Ia1 to Ia4:

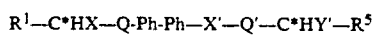    Ia1

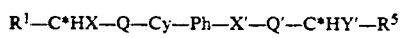    Ia2

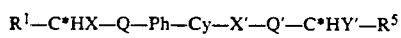    Ia3

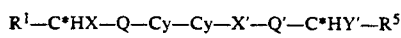    Ia4

Amongst these, those of the formulae Ia1 and Ia3 are particularly preferred.

The preferred compounds of the formula Ib include those of the part formulae Ib1 to Ib4:

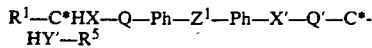    Ib1

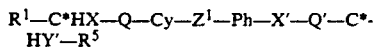    Ib2

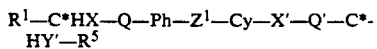    Ib3

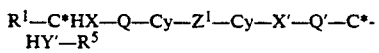    Ib4

Amongst these, those of the formulae Ib1 and Ib3 are particularly preferred.

The preferred compounds of the formula Ic include those of the part formulae Ic1 to Ic4:

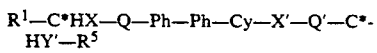    Ic1

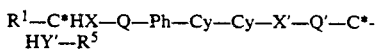    Ic2

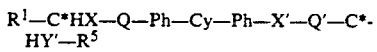    Ic3

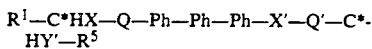    Ic4

The preferred compounds of the formula Id include those of the part formulae Id1 to Id3:

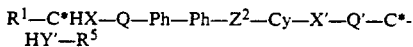    Id1

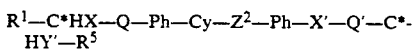    Id2

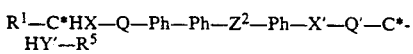    Id3

The preferred compounds of the formula Ie include those of the part formulae Ie1 to Ie5:

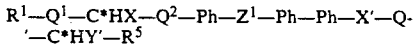    Ie1

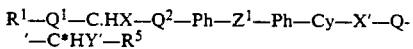    Ie2

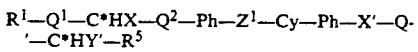    Ie3

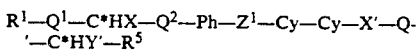    Ie4

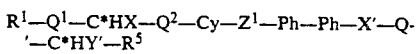    Ie5

Compounds of the formulae above and below wherein $R^1$ and $R^5$ are each independently of one another alkyl are preferred.

In the preferred compounds of the formulae above and below, the alkyl radicals, in which one $CH_2$— group (alkoxy or oxaalkyl) can also be replaced by an 0 atom, can be straight-chain or branched. Preferably, they have 5, 6, 7, 8, 9 or 10 C atoms and are accordingly preferably pentyl, hexyl, heptyl, octyl, nonyl, decyl, pentoxy, hexoxy, heptoxy, octoxy, nonoxy or decoxy, or furthermore ethyl, propyl, butyl, undecyl, dodecyl, propoxy, ethoxy, butoxy, undecoxy, dodecoxy, 2-oxapropyl (=2-methoxymethyl), 2- (=ethoxymethyl) or 3-oxabutyl (=2-methoxypentyl), 2-, 3- or 4-oxapentyl, 2-, 3-, 4- or 5-oxahexyl or 2-, 3-, 4-, 5- or 6-oxaheptyl.

$A^2$, $A^3$ and $A^4$ are preferably Cy or Ph. In the compounds of the formulae above and below, Ph is preferably a 1,4-phenylene (Phe), a pyrimidine-2,5-diyl (Pyr), a pyridine-2,5-diyl (Pyn), a pyrazine-3,6-diyl or a pyridazine-2,5-diyl group, particularly preferably Phe, Pyr or Pyn. The compounds according to the invention preferably contain not more than one 1,4-phenylene group wherein one or two CH— groups are replaced by N. Cy preferably denotes a 1,4-cyclohexylene group. However, compounds of the formula I where one of the groups $A^2$, $A^3$ and $A^4$ is a 1,4-cyclohexylene group which is substituted by CN in the 1- or 4-position and the nitrile group is in the axial position, that is to say the group $A^2$, $A^3$ or $A^4$ has the following configuration:

are particularly preferred.

Compounds of the formula I and the above part formulae which contain a —Ph—Ph— grouping are particularly preferred. —Ph—Ph— is preferably —Phe—Phe—, Phe—Pyr or Phe—Pyn. The groups

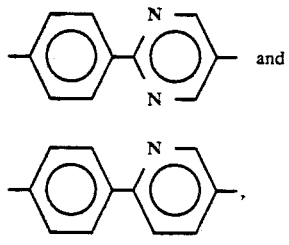

and furthermore 4,4'-biphenylyl which is unsubstituted or mono- or polysubstituted by fluorine are particularly preferred.

$Z^1$ and $Z^2$ are preferably single bonds, and secondly are preferably —O—CO—, —CO—O—, —C≡C— or —CH$_2$CH$_2$— groups.

$Z^1$ is particularly preferably —CO—O— —O—CO—, —C≡C— or —CH$_2$CH$_2$—, or in particular the —CH$_2$CH$_2$— or the —C≡C— group.

X in the compounds of the formulae above and below is halogen, CN or CH$_3$, preferably Cl or CH$_3$.

The preferred meaning of Q is alkylene with 1 or 2 C atoms, —O—, —O—CO— and —COO—.

Compounds of the formulae above and below with branched groups $R^1$ or $R^5$ may be of importance. Branched groups of this type as a rule contain not more than two chain branchings. $R^1$ or $R^5$ is preferably a straight-chain group or a branched group with not more than one chain branching.

Preferred branched radicals are isopropyl, 2-butyl (=1-methylpropyl), isobutyl (=2-methylpropyl), tert.-butyl, 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy, 2-oxa-3-methylbutyl and 3-oxa-4-methylpentyl.

X' is preferably —CO—O—, —O—CO—, —CH=CH—COO—(trans) or a single bond. —CO—O—, —O—CO— or a single bond are particularly preferred.

Q' is preferably —CH$_2$—, —CH$_2$CH$_2$—, —CH$_2$CH$_2$CH$_2$— or a single bond, particularly preferably a single bond.

Y' is preferably CH$_3$, —CN or Cl, particularly preferably Cl or CH$_3$.

$R^5$ is preferably straight-chain or branched alkyl with 1 to 10, in particular with 1 to 7, C atoms.

Of the compounds of the formula I, those in which X and Y' are not simultaneously methyl are preferred.

Of the compounds of the formula I and Ia to Iq, those in which at least one of the radicals contained therein has one of the preferred meanings given are preferred.

A small group of particularly preferred meanings for the optically active radicals $R^1$ (or $R^1$—C*HX—Q) and —X'—Q'—C*HY'—$R^5$ in these preferred compounds is given below:

—O—C*HCH$_3$—n—alkyl, —O—CH$_2$—C*HCH$_3$—n—alkyl, —O—CH$_2$—CH$_2$— C*HCH$_3$—n—alkyl, —O—CH$_2$—CH$_2$—CH$_2$—C*HCH$_3$—n—alkyl, —C*HCH$_3$—n—alkyl, —CH$_2$—C*HCH$_3$—n—alkyl, —COO—C*CHCH$_3$—n—alkyl—, —COO—CH$_2$—C*HCH$_3$—n—alkyl, —O—C*HCH$_3$—COO—n—alkyl, —O—C*HCH$_3$—CH$_2$—O—n—alkyl, —OCO—C*HCl—CHCH$_3$—CH$_3$, —OCO—C*HCl—C*HCH$_3$—C$_2$H$_5$, —OCO—C*HCl—CH$_2$—CHCH$_3$—CH$_3$, —OCO—C*HCl—C(CH$_3$)$_3$, —COO—C*HCH$_3$—COO—n—alkyl, —O—CO—C*HCH$_3$—O—n—alkyl, —OCH$_2$—C*HCH$_3$—O—n—alkyl, —COO—C*HCH$_3$—CH$_2$—O—n—alkyl, —OC*HCH$_3$—CH$_2$—COO—n—alkyl, —COO—C*HCH$_3$—CH$_2$—COO—n—alkyl, —OCH$_2$—C*HCH$_3$—COO—n—alkyl, —COO—CH$_2$—C*HCH$_3$—COO—n—alkyl.

In the preferred compounds of the formula I wherein —X'—Q'—C*HY'—$R^5$ is an optically active radical $R^1$—C*HX—Q can be identical to or different from —X'—Q'—C*HY'—$R^5$.

Preferably, —X'—Q'—C*HY'—$R^5$ and $R^1$—C*HX—Q differ and have a meaning given as preferred for —X'—Q'—C*HY'—$R^5$.

A small group of particularly preferred compounds of the formulae I1 to I23 is listed below:

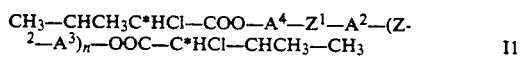

I1

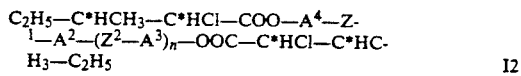

I2

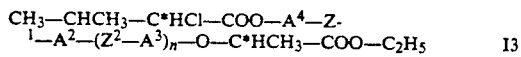

I3

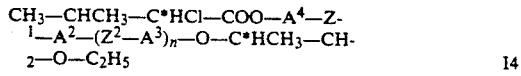

I4

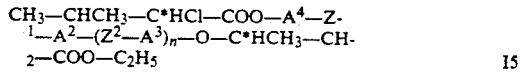

I5

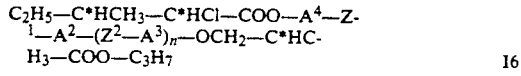

I6

$CH_3-CHCH_3-C^*HCl-COO-A^4-Z^1-A^2-(Z^2-A^3)_n-OCH_2-C^*HCH_3-C_2H_5$    I7

$C_2H_5-C^*HCH_3-C^*HCl-COO-A^4-Z^1-A^2-(Z^2-A^3)_n-O-C^*HCH_3-C_6H_{13}$    I8

$C_2H_5-C^*HCH_3-C^*HCl-COO-A^4-Z^1-A^2-(Z^2-A^3)_n-O-C^*HCH_3-C_6C_{13}$    I9

$CH_3-CHCH_3-C^*HCl-COO-A^4-Z^1-A^2-(Z^2-A^3)_n-COO-C^*HCH_3-COO-C_2H_5$    I10

$C_2H_5-C^*HCH_3-C^*HCl-COO-A^4-Z^1-A^2-(Z^2-A^3)_n-COO-CH_2-C^*HCH_3-COO-C_3H_7$    I11

$C_2H_5-C^*HCH_3-C^*HCl-COO-A^4-Z^1-A^2-(Z^2-A^3)_n-OCH_2-C^*HCH_3-O-C_2H_5$    I12

$CH_3-CHCH_3-C^*HCl-COO-A^4-Z^1-A^2-(Z^2-A^3)_n-COO-C^*HCH_3-CH_2-COO-C_4H_9$    I13

$C_2H_5-C^*HCH_3-C^*HCl-COO-A^4-Z^1-A^2-(Z^2-A^3)_n-OCO-C^*HCl-t-C_4H_9$    I14

$C_2H_5-C^*HCH_3-C^*HCl-COO-A^4-Z^1-A^2-(Z^2-A^3)_n-OOC-C^*HCl-i-C_4H_9$    I15

$C_2H_5-C^*HCH_3-C^*HCl-COO-A^4-Z^1-A^2-(Z^2-A^3)_n-O-C^*HCH_3-COO-C_2H_5$    I16

$CH_3-CHCH_3-C^*HCl-COO-A^4-Z^1-A^2-(Z^2-A^3)_n-OCH_2-C^*HCH_3-C_2H_5$    I17

$C_2H_5-C^*HCH_3-C^*HCl-COO-A^4-Z^1-A^2-(Z^2-A^3)_n-O-C^*HCH_3-C_6H_{13}$    I18

$C_3H_7-OOC-C^*HCH_3-O-A^4-Z^1-A^2-(Z^2-A^3)_n-OC^*HCH_3-COO-C_3H_7$    I19

$C_3H_7-O-CH_2-C^*HCH_3-O-A^4Z^1-A^2-(Z^2-A^3)_n-OC^*HCH_3-CH_2O-C_3H_7$    I20

$CH_2H_5-OOC-C^*HCH_3-OOC-A^4-Z^1-A^2-(Z^2-A^3)_n-COO-C^*CHCH_3-COO-C_2H_5$    I21

$C_2H_5-O-C^*HCH_3-COO-A^4Z^1-A^2-(Z^2-A^3)_n-OOC-C^*HCH_3-O-C_2H_5$    I22

$C_2H_5-O-C^*HCH_3-CH_2-O-A^4-Z^1-A^2-(Z^2-A^3)_n-O-CH_2-C^*HCH_3-O-C_2H_5$    I23

Optically active compounds of the formula I characterized by the formulae $R^1-C^*HX-COO-A^4-Z^1-A^2-(Z^2-A^3)_n-OOC-C^*HY'-R^5$ and    55

$R^1-C^*HX-COO-A^4-Z^1-A^2-OOC-C^*HY'-R^5$ wherein $R^1$, $R^5$, n, X, Y', $A^2$, $A^3$, $A^4$, $Z^1$ and $Z^2$ have the meaning given in claim 1, are particularly preferred.

Compounds of the above formulae wherein X and Y' are halogen, compounds of the above formulae wherein $A^4$ and $A^2$ are 1,4-phenylene and corresponding compounds wherein $Z^1$ is a single bond are particularly preferred.

In the compounds of the formula I and in the part formulae above and below, $-A^4-Z^1-A^2-(Z^2-A^3)_n-$ is preferably a group of the following formulae 1 to 16 or a mirror image thereof:

(p = 1, 2, 3, or 4;
q = 0, 1, 2, 3 or 4)

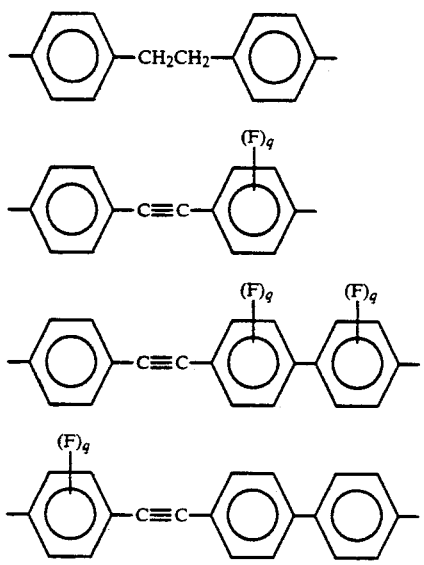

Groups of the formulae 1, 5, 7, 9, 10, 11, 12, 13 and 14, especially those of the formulae 5 and 7, are particularly preferred.

Those of the abovementioned formulae which contain one or more groups Dio, Dit, Pip and/or Pyr in each case include the two possible 2,5-position isomers (Dio, Dit, Pyr) or 1,4-position isomers (Pip).

The compounds of the formula I are prepared by methods which are known per se, such as are described in the literature (for example in the standard works, such as Houben-Weyl, Methoden der Organischen Chemie (Methods of Organic Chemistry), Georg-Thieme-Verlag, Stuttgart), and in particular under reaction conditions which are known and suitable for the reactions mentioned. It is thereby possible also to utilize variants which are known per se and are not mentioned here in more detail.

If desired, the starting substances can also be formed in situ such that they are not isolated from the reaction mixture but are immediately reacted further to give the compounds of the formula I.

The compounds of the formula I can thus be prepared by reducing a compound which otherwise corresponds to the formula I but contains one or more reducible groups and/or C—C bonds instead of H atoms.

Preferred possible reducible groups are —CH=CH— groups, and furthermore, for example, free or esterified hydroxyl groups, aromatically bonded halogen atoms or carbonyl groups. Preferred starting substances for the reduction correspond to the formula I, but can also contain a —CH=CH— group instead of a —CH₂CH₂— group and/or a —CO— group instead of a —CH₂— group and/or a free or a functionally modified OH group (for example in the form of its p-toluenesulfonate) instead of an H atom.

The reduction can be carried out, for example, by catalytic hydrogenation at temperatures between about 0° and about 200° under pressures between about 1 and 200 bar in an inert solvent, for example an alcohol, such as methanol, ethanol or isopropanol, an ether, such as tetrahydrofuran (THF) or dioxane, an ester, such as ethyl acetate, a carboxylic acid, such as acetic acid, or a hydrocarbon, such as cyclohexane. Catalysts which are advantageously suitable are noble metals, such as Pt or Pd, which can be used in the form of oxides (for example PtO₂ or PdO), on a support (for example Pd-on-charcoal, calcium carbonate or strontium carbonate) or in finely divided form.

Ketones can also be reduced to the corresponding compounds of the formula I which contain alkyl groups and/or —CH₂CH₂— bridges by the methods of Clemmensen (with zinc, zinc amalgam or tin and hydrochloric acid, advantageously in aqueous-alcoholic solution or in a heterogeneous phase system with water/toluene at temperatures between about 80° and 120°) or Wolff-Kishner (with hydrazine, advantageously in the presence of an alkali, such as KOH or NaOH, in a high-boiling solvent, such as diethylene glycol or triethylene glycol, at temperatures between about 100° and 200°).

Reductions with complex hydrides are furthermore possible. For example, arylsulfonyloxy groups can be reduced by reduction with LiAlH₄, and in particular p-toluenesulfonyloxymethyl groups can be reduced to methyl groups, advantageously in an inert solvent, such as diethyl ether or THF, at temperatures between about 0° and 100°. Double bonds (also in the presence of CN groups!) can be hydrogenated with NaBH₄ or tributyltin hydride in methanol; thus, for example, the corresponding cyclohexane derivatives are formed from 1-cyanocyclohexene derivatives.

Esters of the formula I can also be obtained by esterification of corresponding carboxylic acids (or their reactive derivatives) with alcohols or phenols (or their reactive derivatives).

Suitable reactive derivatives of the carboxylic acids mentioned are, in particular, the acid halides, above all the chlorides and bromides, and furthermore the anhydrides, for example also mixed anhydrides, azides or esters, in particular alkyl esters with 1-4 C atoms in the alkyl group.

Possible reactive derivatives of the alcohols or phenols mentioned are, in particular, the corresponding metal alcoholates or phenolates, preferably of an alkali metal, such as Na or K.

The esterification is advantageously carried out in the presence of an inert solvent. Particularly suitable solvents are ethers, such as diethyl ether, di-n-butyl ether, THF, dioxane or anisole, ketones, such as acetone, butanone or cyclohexanone, amides, such as DMF or phosphoric acid hexamethyltriamide, hydrocarbons, such as benzene, toluene or xylene, halogenohydrocarbons, such as carbon tetrachloride or tetrachloroethylene, and sulfoxides, such as dimethyl sulfoxide or sulfolane. Water-immiscible solvents can at the same time be advantageously used for removal, by azeotropic distillation, of the water formed during the esterification. An excess of an organic base, for example pyridine, quinoline or triethylamine, can occasionally also be used as the solvent for the esterification. The esterification can also be carried out in the absence of a solvent, for example by simply heating the components in the presence of sodium acetate. The reaction temperature is usually between —50° and +250°, preferably between —20° and +80°. At these temperatures, the esterification reactions are as a rule ended after 15 minutes to 48 hours.

In detail, the reaction conditions for the esterification largely depend on the nature of the starting substances used. Thus, a free carboxylic acid is as a rule reacted with a free alcohol or phenol in the presence of a strong acid, for example a mineral acid, such as hydrochloric acid or sulfuric acid. A preferred reaction procedure is reaction of an acid anhydride or, in particular, an acid chloride with an alcohol, preferably in a basic medium, bases which are of particular importance being alkali metal hydroxides, such as sodium or potassium hydroxide, alkali metal carbonates or bicarbonates, such as sodium carbonate, potassium carbonate or potassium bicarbonate, alkali metal acetates, such as sodium or potassium acetate, alkaline earth metal hydroxides, such as calcium hydroxide, or organic bases, such as triethylamine, pyridine, lutidine, collidine or quinoline. Another preferred embodiment of the esterification comprises a procedure in which the alcohol or phenol is first converted into the sodium or potassium alcoholate or phenolate, for example by treatment with ethanolic sodium hydroxide solution or potassium hydroxide solution, this alcoholate or phenolate is isolated and suspended in acetone or diethyl ether, together with sodium bicarbonate or potassium carbonate, with stirring, and a solution of the acid chloride or anhydride in diethyl ether, acetone or DMF is added to this suspension, advantageously at temperatures between about $-25°$ and $+20°$.

Dioxane derivatives or dithiane derivatives of the formula I are advantageously prepared by reaction of a corresponding aldehyde (or one of its reactive derivatives) with a corresponding 1,3-diol or a corresponding 1,3-dithiol (or one of their reactive derivatives), preferably in the presence of an inert solvent, such as benzene or toluene, and/or a catalyst, for example a strong acid, such as sulfuric acid or benzene- or p-toluenesulfonic acid, at temperatures between 20° and about 150°, preferably between 80° and 120°. Suitable reactive derivatives of the starting substances are above all acetals.

The aldehydes and 1,3-diols or 1,3-dithiols mentioned and their reactive derivatives are known in some cases, and they can all be prepared without difficulty from compounds which are known from the literature by standard processes of organic chemistry. For example, the aldehydes are obtainable by oxidation of corresponding alcohols or by reduction of corresponding carboxylic acids or their derivatives, the diols are obtainable by reduction of corresponding diesters and the dithiols are obtainable by reaction of corresponding dihalides with NaSH.

To prepare nitriles of the formula I, corresponding acid amides, for example those which contain a $CONH_2$-group instead of the radical X, can be dehydrated. The amides are obtainable, for example, from corresponding esters or acid halides by reaction with ammonia. Examples of suitable dehydrating agents are inorganic acid chlorides, such as $SOCl_2$, $PCl_3$, $PCl_5$, $POCl_3$, $SO_2Cl_2$ or $COCl_2$, and furthermore $P_2O_5$, $P_2S_5$, $AlCl_3$ (for example as double compounds with NaCl), aromatic sulfonic acids and sulfonic acid halides. The reaction here can be carried out in the presence or absence of an inert solvent at temperatures between about 0° and 150°; possible solvents are, for example, bases, such as pyridine or triethylamine, aromatic hydrocarbons, such as benzene, toluene or xylene, or amides, such as DMF.

To prepare the abovementioned nitriles of the formula I, corresponding acid halides, preferably the chlorides, can also be reacted with sulfamide, advantageously in an inert solvent, such as tetramethylene sulfone, at temperatures between about 80° and 150°, preferably at 120°. After customary working up, the nitriles can be isolated directly.

Ethers of the formula I are obtainable by etherification of corresponding hydroxyl compounds, preferably corresponding phenols, the hydroxyl compound advantageously first being converted into a corresponding metal derivative, for example into the corresponding alkali metal alcoholate or alkali metal phenolate by treatment with NaH, $NaNH_2$, NaOH, KOH, $Na_2CO_3$ or $K_2CO_3$. This derivative can then be reacted with the corresponding alkyl halide or sulfonate or dialkyl sulfate, advantageously in an inert solvent, such as acetone, 1,2-dimethoxyethane, DMF or dimethyl sulfoxide, or an excess of aqueous or aqueous-alcoholic NaOH or KOH, at temperatures between about 20° and 100°.

To prepare nitriles of the formula I, corresponding chlorine or bromine compounds of the formula I can also be reacted with a cyanide, advantageously with a metal cyanide, such as NaCN, KCN or $Cu_2(CN)_2$, for example in the presence of pyridine in an inert solvent, such as DMF or N-methylpyrrolidone, at temperatures between 20° and 200°.

The optically active compounds of the formula I are obtained by using corresponding optically active starting materials and/or by resolving the optical antipodes by known methods by means of chromatography.

The phases according to the invention contain at least one and preferably at least two compounds of the formula I. Chiral tilted smectic liquid crystal phases in which the achiral base mixture, in addition to compounds of the formula I, contains at least one other component with a negative or relatively low positive dielectric anisotropy are particularly preferred. This/these other component(s) of the chiral base mixture can make up 1 to 50%, preferably 10 to 25%, of the base mixture. Suitable other components of relatively low positive or negative dielectric anisotropy are compounds of the part formulae Va to Vp:

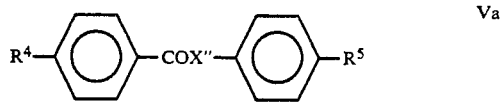

Va

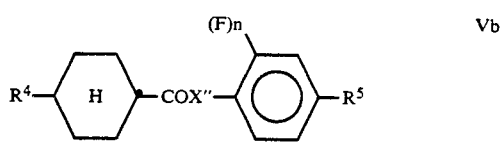

Vb

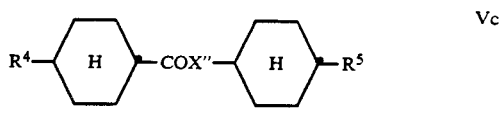

Vc

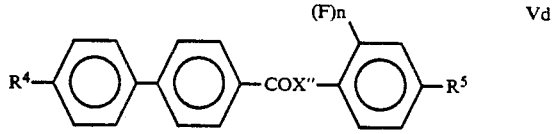

Vd

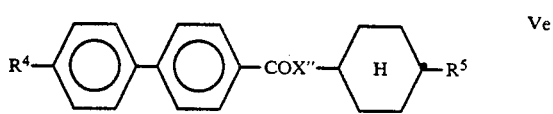

Ve

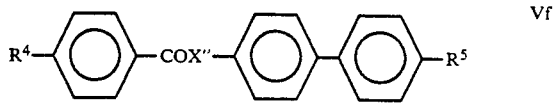

Vf

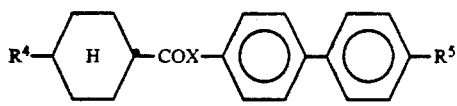 Vg

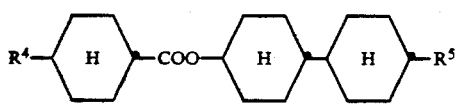 Vh

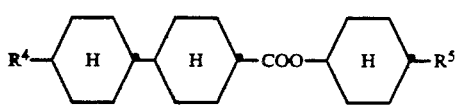 Vi

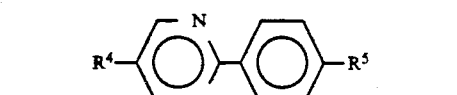 Vj

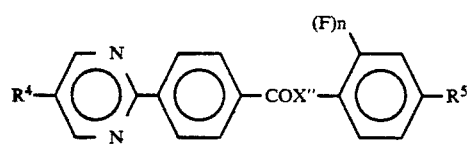 Vk

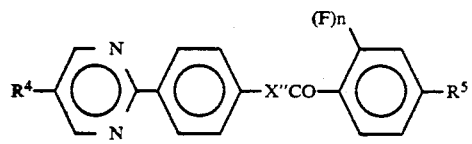 Vl

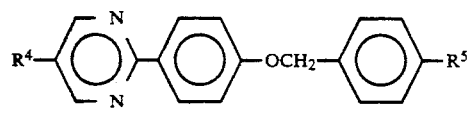 Vm

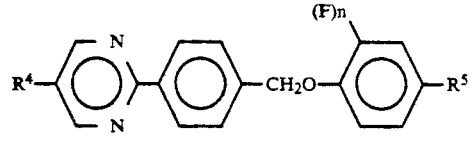 Vn

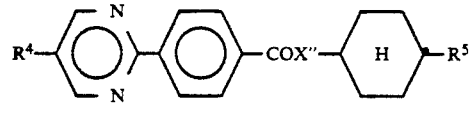 Vo

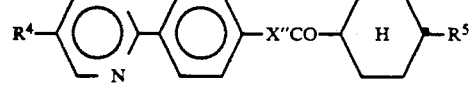 Vp $R^4$ and $R^5$ are each preferably straight-chain alkyl, alkoxy, alkanoyloxy or alkoxycarbonyl with in each case 3 to 12 C atoms. X" is O or S, preferably O. n is 0 or 1.

The compounds of the part formulae Va, Vb, Vd and Vf wherein $R^4$ and $R^5$ are each straight-chain alkyl or alkoxy with in each case 5 to 10 C atoms are particularly preferred.

The compounds of the part formulae Vc, Vh and Vi are suitable as additives for reducing the melting point and are usually added to the base mixtures in amounts of not more than 5%, preferably 1 to 3%. $R^4$ and $R^5$ in the compounds of the part formulae Vc, Vh and Vi are preferably straight-chain alkyl with 2 to 7, preferably 3 to 5, C atoms. Another class of compound which is suitable for lowering the melting point in the phases according to the invention is that of the formula

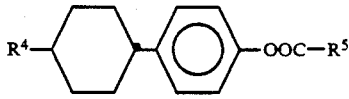

wherein $R^4$ and $R^5$ have the meaning given as preferred for Vc, Vh and Vi.

Other suitable components with negative dielectric anisotropy are furthermore compounds containing the structural element M, N or O.

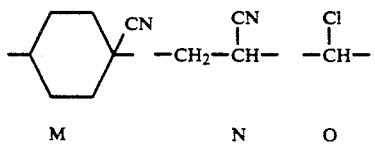

M  N  O

Preferred compounds of this type correspond to the formulae VIb and VIc:

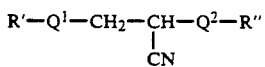 VIb $R'-Q^3-Q^4-R'''$ VIc

R' and R" are each preferably straight-chain alkyl or alkoxy groups with in each case 2 to 10 C atoms. $Q^1$ and $Q^2$ are each 1,4-phenylene, trans-1,4-cyclohexylene, 4,4'-biphenylyl, 4-(trans-4-cyclohexyl)-phenyl, or trans,trans-4,4'-bicyclohexyl, or one of the groups $Q^1$ and $Q^2$ is also a single bond.

$Q^3$ and $Q^4$ are each 1,4-phenylene, 4,4'-biphenylyl or trans-1,4-cyclohexylene. One of the groups $Q^3$ and $Q^4$ can also be 1,4-phenylene, at least one CH-group being replaced by N. R''' is an optically active radical with an asymmetric carbon atom with the structure

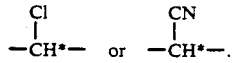

Particularly preferred compounds of the formula VIc are those of the formula VIc':

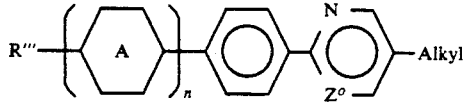

wherein A is 1,4-phenylene or trans-1,4-cyclohexylene, Z° is CH or N and n is 0 or 1.

The compounds of the formula I are also suitable as components of nematic liquid crystal phases, for example for avoiding reverse twist.

These liquid crystal phases according to the invention consist of 2 to 25, preferably 3 to 15, components, at least one of which is a compound of the formula I. The other constituents are preferably selected from the nematic or nematogenic substances, in particular the known substances, from the classes of azoxybenzenes, benzylideneanilines, biphenyls, terphenyls, phenyl or cyclohexyl benzoates, phenyl or cyclohexyl cyclohexanecarboxylates, phenylcyclohexanes, cyclohexylbiphenyls, cyclohexylcyclohexanes, cyclohexylnaphthalenes, 1,4-biscyclohexylbenzenes, 4,4'-bis-cyclohexylbiphenyls, phenyl-or cyclohexylpyrimidines, phenyl- or cyclohexylpyridazines and N-oxides thereof, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, optionally halogenated stilbenes, benzyl phenyl ethers, tolanes and substituted cinnamic acids.

The most important compounds possible as constituents of such liquid crystal phases can be characterized by the formula I'

R'—L—G—E—R"  I' wherein L and E are each a carbo- or heterocyclic ring system from the group formed by 1,4-disubstituted benzene and cyclohexane rings, 4,4'-disubstituted biphenyl, phenylcyclohexane and cyclohexylcyclohexane systems, 2,5-disubstituted pyrimidine and 1,3-dioxane rings, 2,6-disubstituted naphthalene, di- and tetrahydronaphthalene, quinazoline and tetrahydroquinazoline, G is

| —CH=CH— | —N(O)=N— |
| —CH=CY— | —CH=N(O)— |
| —C≡C— | —CH$_2$—CH$_2$— |
| —CO—O— | —CH$_2$—O— |
| —CO—S— | —CH$_2$—S— |
| —CH=N— | —COO—Phe—COO— | or a C—C single bond,

Y is halogen, preferably chlorine, or —CN and R' and R" are alkyl, alkoxy, alkanoyloxy, alkoxycarbonyl or alkoxycarbonyloxy with up to 18, preferably up to 8, carbon atoms, or one of these radicals is also CN, NC, NO$_2$, CF$_3$, F, Cl or Br.

In most of these compounds, R' and R" differ from one another, one of these radicals usually being an alkyl or alkoxy group. However, other variants of the envisaged substituents are also customary. Many such substances or mixtures thereof are commercially available. All of these substances are obtainable by methods which are known from the literature.

The phases according to the invention contain about 0.1 to 99%, preferably 10 to 95%, of one or more compounds of the formula I. Liquid crystal phases according to the invention which contain 0.1–40%, preferably 0.5–30%, of one or more compounds of the formula I are furthermore preferred.

The phases according to the invention are prepared in the customary manner. As a rule, the components are dissolved in one another, advantageously at elevated temperature.

The liquid crystal phases according to the invention can be modified by suitable additives such that they can be used in all the types of liquid crystal display elements which have been disclosed to date.

Such additives are known to the expert and are described in detail in the literature. For example, it is possible to add conductive salts, for example ethyldimethyl-dodecyl-ammonium 4-hexyloxybenzoate, tetrabutylammonium tetraphenylboranate or complex salts of crown ethers (compare, for example, I. Haller et al., Mol. Cryst. Liq. Cryst. Volume 24, pages 249-258 (1973)) to improve the conductivity, pleochroic dyestuffs to prepare coloured guest-host systems or substances for modifying the dielectric anisotropy, the viscosity and/or the orientation of the nematic phases.

Such substances are described, for example, in German Offenlegungsschriften 2,209,127, 2,240,864, 2,321,632, 2,338,281, 2,450,088, 2,637,430, 2,853,728 and 2,902,177.

The following examples are intended to illustrate the invention, without limiting it. M.p.=melting point, c.p.=clear point. Percentages above and below are percentages by weight; all the temperatures are given in degrees Celsius. "Customary working up" means: water is added, the mixture is extracted with methylene chloride, the organic phase is separated off, dried and evaporated and the product is purified by crystallization and/or chromatography.

Other abbreviations furthermore have the following meanings: C: crystalline solid state, S: smectic phase (the index characterizes the phase type), N: nematic state, Ch: cholesteric phase, I: isotropic phase. The number between two symbols indicates the transition temperature in degrees Celsius.

EXAMPLE 1

A mixture of 8 g of (S,S)-3-methyl-2-chloropentanoic acid, 16 g of optically active p-[5—(2,6-dimethylheptyl)-pyrimidin-2-yl]phenol [obtainable by condensation, known from the literature, of (S)-1,1,3,3-tetraethoxy-2-(2,6-dimethylheptyl)-propane with 4-hydroxyphenylamidine hydrochloride], 11.6 g of N,N-dicyclohexylcarbodiimide, 0.6 g of 4-N,N-dimethylaminopyridine and 300 ml of methylene chloride is stirred overnight at room temperature. After the urea derivative which has precipitated has been filtered off, the filtrate is washed with dilute hydrochloric acid and H$_2$O and the organic phase is worked up in the customary manner. p-[5-(2,6-Dimethylheptyl)-pyrimidin-2-yl]-phenyl (S,S)-3-methyl-2-chloropentanoate is obtained.

EXAMPLE 2

3.1 g of dicyclohexylcarbodiimide in 5 ml of methylene chloride are added dropwise to a mixture of 4.9 g of optically active hydroquinone 4-cyano-4—(3,7-dimethyloctyl)-cyclohexanecarboxylate (obtainable by esterification of 4-cyano-4-(3,7-dimethyloctyl)-cyclohexanecarboxylic acid with hydroquinone monobenzyl ether and subsequent removal of the benzyl group by catalytic hydrogenation), 1.87 g of optically active 2-chloro-3-methylbutyric acid and 170 mg of 4-N,N'-dimethylaminopyridine in 30 ml of methylene chloride at 0° with exclusion of moisture. After the mixture has been stirred at room temperature for 12 hours and filtered and the filtrate has been worked up in the customary manner, optically active p-(4-cyano-4-(3,7-dimethyloctyl)-cyclohexylcarbonyloxy)-phenyl 2-chloro-3-methylbutyrate is obtained.

The following compounds are prepared analogously:
p-(4-cyano-4-(2-methylbutyl)-cyclohexylcarbonyloxy)-phenyl 2-chloro-3-methylbutyrate,
p-(4-cyano-4-(2-methylbutyl)-cyclohexyl)-phenyl 2-chloro-3-methylbutyrate,
p-(4-cyano-4-(3,7-dimethyloctyl)-cyclohexyl)-phenyl 2-chloro-3-methylbutyrate,
p-(p-(3-methylpentyl)-benzoyloxy)-phenyl 2-chloro-3-methylbutyrate, p-(trans-4-(4,8-dimethylnonyl)-cyclohexanecarbonyloxy)phenyl 2-chloro-3-methylbutyrate.

EXAMPLE 3

An excess of (S,S)-3-methyl-2-chloropentanoic acid is reacted with 4,4'-bis-hydroxybiphenyl analogously to Example 1. Customary working up gives optically active 4,4'-bis-(2-chloro-3-methylpentanoyloxy)-biphenyl.

The following compounds are prepared analogously:
4,4'-bis-(2-chloro-3-methylbutyryloxy)-biphenyl, m.p. 92°,
4,4'-bis-(2-chloro-4-methylpentanoyloxy)-biphenyl, m.p. 70°,
4,4'-bis-(2-chloro-3-methylbutyryloxy)-trans,trans-cyclohexylcyclohexane
4,4'-bis-(2-chloro-4-methylpentanoyloxy)-trans,transcyclohexylcyclohexane
4,4'-bis-(2-chloro-3-methylpentanoyloxy)-trans,transcyclohexylcyclohexane.

EXAMPLE 4

A mixture of 5.3 g of p-[p-(4-cyano-4-(2-methylbutyl)-cyclohexyl)-phenyl]-phenol (obtainable by alkaline ether cleavage from r-1-cyano-cis-4-(4'-propyloxybiphenyl-4-yl)-1-(2-methylbutyl)-cyclohexane with potassium tert.-butylate in NMP at 180°), 1.9 g of optically active 2-chloro-3-methyl-butyric acid and 170 g of DMAP are suspended in 40 ml of CH$_2$Cl$_2$. 3.1 g of DCC in 5 ml of CH$_2$Cl$_2$ are then added dropwise and the mixture is stirred at room temperature for 12 hours. After removal of the dicyclohexylurea and customary working up, optically active 4'-(4-cyano-4-(2-methylbutyl)-cyclohexyl)-biphenyl-4-yl 2-chloro-3-methylbutyrate is obtained.

EXAMPLE 5

Esterification of optically active 4—(4'-(2-octyloxy)-biphenyl-4-yl)-1-cyano-1-(2-hydroxypropyl)cyclohexane (obtainable from 4-(4'-(2-octyloxy)-biphenyl-4-yl)-cyclohexanecarbonitrile by alkylation with optically active propylene oxide and lithium diisopropylamide, as the base) with optically active 2-chloro-3-methylbutyric acid gives optically active 1-[4-cis-(4'-(2-octyloxy)-biphenyl-4-yl)-r-1-cyanocyclohexyl]-2-propyl 2-chloro-3-methylbutyrate.

EXAMPLE 6

A solution of optically active 4-(2-octyloxy)-4'-hydroxybiphenyl in toluene is added dropwise to a solution of 2.4 g of optically active α-pentyloxypropionyl chloride in 25 ml of pyridine and the mixture is heated under reflux for 2 hours. Customary working up gives 4-(2-octyloxy)-4'-(α-pentyloxypropanoyloxy)-biphenyl.

The following compounds are prepared analogously:
4,4'-bis-(α-pentyloxypropanoyloxy)-biphenyl,
4,4'-bis-(α-butyloxypropanoyloxy)-biphenyl,
4,4'-bis-(α-propyloxypropanoyloxy)-biphenyl,
4,4'-bis-(α-ethyloxypropanoyloxy)-biphenyl.

EXAMPLE 7

0.035 mol of 4,4'-bis-hydroxybiphenyl, 0.07 mol of (S)-3,7-dimethyloctanoic acid and 1 g of 4-N,N'-dimethylaminopyridine (DMAP) are dissolved in 150 ml of toluene. A solution of 16.0 g of dicyclohexylcarbodiimide (DCC) in 40 ml of toluene is added dropwise, the mixture is stirred overnight and chromatographed with toluene over silica gel and the product is recrystallized to give optically active 4,4'-bis-(3,7-dimethyloctanoyloxy)-biphenyl, m.p. 72°–73°.

EXAMPLE 8

25 mmol of 4,4''-terphenyldicarboxylic acid (obtainable by reaction of dibromoterphenyl with CuCN in NMP and hydrolysis of the dinitrile with KOH in diethylene glycol), 7.9 g of (S)-3,7-dimethyloctanol and 0.12 g of DMAP are taken in 40 ml of toluene. A solution of 9.9 g of DCC in 15 ml of toluene is added dropwise at room temperature, with stirring, the mixture is stirred overnight and chromatographed with toluene on silica gel and the product is recrystallized to give 4,4''-bis-(3,7-dimethyloctyloxycarbonyl)-p-terphenyl.

EXAMPLE 9

80.5 g (0.3 mol) of (S)-3,7-dimethyl-1-iodoctane are added dropwise to a solution of 16.2 g (0.3 mol) of sodium methylate and 24.8 g (0.1 mol) of 1-fluoro-2,5-di(4-hydroxyphenyl)-benzene in 150 ml of methanol at the boiling point. After 5 hours, the mixture is worked up in the customary manner. Recrystallization gives pure 1-fluoro-2,5-di-[4-(3,7-dimethyloctyloxy)-phenyl]-benzene.

EXAMPLE 10

S,S-3-Methyl-2-chloropentanoic acid is esterified in the presence of DCC with optically active 2-(p-hydroxyphenyl)-3-(3-methylpentyl)-pyridine [which can be prepared from 2-(p-methoxyphenyl)-3-(3-methylpentyl)pyridine by basic ether cleavage with potassium tert.butylate in NMP at 180° C.] in accordance with Example 1 and the mixture is worked up in the customary manner. p-[4-(3-Methylpentyl)-pyridin-2-yl]-phenyl (S,S)-3-methyl-2-chloropentanoate is obtained.

EXAMPLE A

A liquid crystal phase consisting of
3% of 2-p-hexyloxyphenyl-5-heptylpyrimidine
3% of 2-p-heptyloxyphenyl-5-heptylpyrimidine
3% of 2-p-octyloxyphenyl-5-heptylpyrimidine
3% of 2-p-nonyloxyphenyl-5-heptylpyrimidine
7% of 2-p-hexyloxyphenyl-5-nonylpyrimidine
23% of 2-p-nonyloxyphenyl-5-nonylpyrimidine
28% of r-1-cyano-cis-4-(4'-butyloxybiphenyl-4-yl)-1-octylcyclohexane
14% of r-1-cyano-cis-4-(4'-heptylbiphenyl-4-yl)-1-hexylcyclohexane
6% of r-1-cyano-cis-4-(trans-4-pentylcyclohexyl)-1-(trans-4-pentylcyclohexyl)-cyclohexane and
10% of 4'-[4-cyano-4-(3,7-dimethylheptyl)-cyclohexyl]-biphenyl-4-yl 2-chloro-3-methylbutyrate
is prepared.

EXAMPLE B

A liquid crystal phase consisting of
3% of 2-p-hexyloxyphenyl-5-heptylpyrimidine
3% of 2-p-heptyloxyphenyl-5-heptylpyrimidine
3% of 2-p-octyloxyphenyl-5-heptylpyrimidine
3% of 2-p-nonyloxyphenyl-5-heptylpyrimidine
7% of 2-p-hexyloxyphenyl-5-nonylpyrimidine
23% of 2-p-nonyloxyphenyl-5-nonylpyrimidine
28% of r-1-cyano-cis-4-(4'-butyloxybiphenyl-4-yl)-1-octylcyclohexane
14% of r-1-cyano-cis-4-(4'-heptylbiphenyl-4-yl)-1-hexylcyclohexane
6% of r-1-cyano-cis-4-(trans-4-pentylcyclohexyl)-1-(trans-4-pentylcyclohexyl)-cyclohexane and 10% of 4,4'-bis-(2-chloro-3-methylbutyryloxy)-biphenyl has a spontaneous polarization of 38 nC/cm$^2$ at room temperature and an S*$_c$/Ch transition at 68°.

EXAMPLE C

A liquid crystal phase consisting of
3% of 2-p-hexyloxyphenyl-5-heptylpyrimidine
3% of 2-p-heptyloxyphenyl-5-heptylpyrimidine
3% of 2-p-octyloxyphenyl-5-heptylpyrimidine
3% of 2-p-nonyloxyphenyl-5-heptylpyrimidine
7% of 2-p-hexyloxyphenyl-5-nonylpyrimidine
23% of 2-p-nonyloxyphenyl-5-nonylpyrimidine
28% of r-1-cyano-cis-4-(4'-butyloxybiphenyl-4-yl)-1-octylcyclohexane
14% of r-1-cyano-cis-4-(4'-heptylbiphenyl-4-yl)-1-hexylcyclohexane
6% of r-1-cyano-cis-4-(trans-4-pentylcyclohexyl)-1-(trans-4-pentylcyclohexyl)-cyclohexane and
10% of p-[5-(3-methylpentyl)-pyridin-2-yl]-phenyl 3-methyl-2-chlorobutyrate
is prepared.

EXAMPLE D

A liquid crystal phase consisting of
3% of 2-p-hexyloxyphenyl-5-heptylpyrimidine
3% of 2-p-heptyloxyphenyl-5-heptylpyrimidine
3% of 2-p-octyloxyphenyl-5-heptylpyrimidine
3% of 2-p-nonyloxyphenyl-5-heptylpyrimidine
7% of 2-p-hexyloxyphenyl-5-nonylpyrimidine
23% of 2-p-nonyloxyphenyl-5-nonylpyrimidine
30% of r-1-cyano-cis-4-(4'-octyloxybiphenyl-4-yl)-1-octylcyclohexane,
15% of r-1-cyano-cis-4-(4'-heptyloxybiphenyl-4-yl)-1-hexyl-cyclohexane
8% of p-(5-nonylpyrimidin-2-yl)-phenyl 3-methyl-2-chlorobutyrate (optically active) and
5% of p-[5-(3,7-dimethyloctyl)-pyrimidin-2-yl]-phenyl 3-methyl-2-chlorobutyrate (optically active)
shows S*$_c$/S$_A$ 57°, S$_A$/Ch 61°, Ch/I 78° and P$_s$=13 nC/cm$^2$.

EXAMPLE E

A liquid crystal phase consisting of
3% of 2-p-hexyloxyphenyl-5-heptylpyrimidine
3% of 2-p-heptyloxyphenyl-5-heptylpyrimidine
3% of 2-p-octyloxyphenyl-5-heptylpyrimidine
3% of 2-p-nonyloxyphenyl-5-heptylpyrimidine
7% of 2-p-hexyloxyphenyl-5-nonylpyrimidine
25% of 2-p-nonyloxyphenyl-5-nonylpyrimidine
30% of r-1-cyano-cis-4-(4'-octyloxybiphenyl-4-yl)-1-octylcyclohexane,
15% of r-1-cyano-cis-4-(4'-heptylbiphenyl-4-yl)-1-hexylcyclohexane
6% of p-(5-heptylpyridin-2-yl)-phenyl 3-methyl-2-chlorobutyrate (optically active) and
5% of 2,5-bis-[p-(3-methyl-2-chlorobutyryloxy)-phenyl]pyridine (optically active)
shows S*$_c$/S$_A$ 61°, S$_A$/Ch 64°, Ch/I 78° and P$_s$=18 nC/cm$^2$.

EXAMPLE F

A liquid crystal phase consisting of
3% of 2-p-hexyloxyphenyl-5-heptylpyrimidine
3% of 2-p-heptyloxyphenyl-5-heptylpyrimidine
3% of 2-p-octyloxyphenyl-5-heptylpyrimidine
3% of 2-p-nonyloxyphenyl-5-heptylpyrimidine
7% of 2-p-hexyloxyphenyl-5-nonylpyrimidine
23% of 2-p-nonyloxyphenyl-5-nonylpyrimidine
28% of r-1-cyano-cis-4-(4'-butyloxybiphenyl-4-yl)-1-octylcyclohexane
14% of r-1-cyano-cis-4-(4'-heptylbiphenyl-4-yl)-1-hexylcyclohexane
6% of r-1-cyano-cis-4-(trans-4-pentylcyclohexyl)-1-(trans-4-pentylcyclohexyl)-cyclohexane and
10% of optically active 4,4'-bis-[1-(ethoxycarbonyl)ethoxy]-biphenyl
shows S*$_c$/S$_A$ 54°, S$_A$/Ch 58°, Ch/I 78° and P$_S$=2 nC/cm$^2$.

EXAMPLE G

A liquid crystal phase consisting of
3% of 2-p-hexyloxyphenyl-5-heptylpyrimidine
3% of 2-p-heptyloxyphenyl-5-heptylpyrimidine
3% of 2-p-octyloxyphenyl-5-heptylpyrimidine
3% of 2-p-nonyloxyphenyl-5-heptylpyrimidine
7% of 2-p-hexyloxyphenyl-5-nonylpyrimidine
23% of 2-p-nonyloxyphenyl-5-nonylpyrimidine
28% of r-1-cyano-cis-4-(4'-butyloxybiphenyl-4-yl)-1-octylcyclohexane
14% of r-1-cyano-cis-4-(4'-heptylbiphenyl-4-yl)-1-hexylcyclohexane
6% of r-1-cyano-1-(trans-4-pentylcyclohexyl)-cis-4-(trans-4-pentylcyclohexyl)-cyclohexane and
10% of optically active 4,4'-bis-(α-butyloxypropanoyloxy)biphenyl
shows S*$_c$/S$_A$ 51°, S$_A$/Ch 53°, Ch/I 76° and P$_s$=2 nC/cm$^2$.

EXAMPLE H

A liquid crystal phase consisting of
3% of 2-p-hexyloxyphenyl-5-heptylpyrimidine
3% of 2-p-heptyloxyphenyl-5-heptylpyrimidine
3% of 2-p-octyloxyphenyl-5-heptylpyrimidine
3% of 2-p-nonyloxyphenyl-5-heptylpyrimidine
7% of 2-p-hexyloxyphenyl-5-nonylpyrimidine
23% of 2-p-nonyloxyphenyl-5-nonylpyrimidine
28% of r-1-cyano-cis-4-(4'-butyloxybiphenyl-4-yl)-1-octylcyclohexane
14% of r-1-cyano-cis-4-(4'-hexylbiphenyl-4-yl)-1-heptylcyclohexane
6% of r-1-cyano-cis-4-(trans-4-pentylcyclohexyl)-1-(trans-4-pentylcyclohexyl)-cyclohexane and
10% of 4,4'-bis-(2-chloro-3-methylbutyryloxy)-trans,trans-cyclohexylcyclohexane
(optically active) shows S*$_c$/S$_a$ 53°, S$_A$/Ch 84°, Ch/I 92° and P$_s$=12 nC/cm$^2$.

EXAMPLE I

A liquid crystal phase consisting of
3% of 2-p-hexyloxyphenyl-5-heptylpyrimidine
3% of 2-p-heptyloxyphenyl-5-heptylpyrimidine
3% of 2-p-octyloxyphenyl-5-heptylpyrimidine
3% of 2-p-nonyloxyphenyl-5-heptylpyrimidine
7% of 2-p-hexyloxyphenyl-5-nonylpyrimidine
23% of 2-p-nonyloxyphenyl-5-nonylpyrimidine
28% of r-1-cyano-cis-4-(4'-butyloxybiphenyl-4-yl)-1-octylcyclohexane
14% of r-1-cyano-cis-4-(4'-hexylbiphenyl-4-yl)-1-heptylcyclohexane
6% of r-1-cyano-cis-4-(trans-4-pentylcyclohexyl)-1-(trans-4-pentylcyclohexyl)-cyclohexane and
10% of 4,4'-bis-(2-chloro-4-methylpentanoyloxy)-trans,trans-cyclohexylcyclohexane
(optically active) shows S*$_c$/S$_A$ 58°, S$_A$/Ch 82°, Ch/I 88° and P$_s$=14 nC/cm$^2$.

EXAMPLE J

A liquid crystal phase consisting of
3% of 2-p-hexyloxyphenyl-5-heptylpyrimidine
3% of 2-p-heptyloxyphenyl-5-heptylpyrimidine
3% of 2-p-octyloxyphenyl-5-heptylpyrimidine
3% of 2-p-nonyloxyphenyl-5-heptylpyrimidine
7% of 2-p-hexyloxyphenyl-5-nonylpyrimidine
23% of 2-p-nonyloxyphenyl-5-nonylpyrimidine
28% of r-1-cyano-cis-4-(4'-butyloxybiphenyl-4-yl)-1-octylcyclohexane
14% of r-1-cyano-cis-4-(4'-hexylbiphenyl-4-yl)-1-heptylcyclohexane
6% of r-1-cyano-cis-4-(trans-4-pentylcyclohexyl)-1-(trans-4-pentylcyclohexyl)-cyclohexane and
10% of 4,4'-bis-(2-chloro-3-methylpentanoyloxy)-trans,trans-cyclohexylcyclohexane
(optically active) shows $S^*_C/S_A$ 55°, $S_A$/Ch 83°, Ch/I 90° and $P_s = 13$ nC/cm².

We claim:

1. Optically active compounds of the formula I $$R^1-C^*HX-Q-A^4-Z^1-A^2-(Z^2-A^3)_n-X'-Q'-C^*HY'-R^5 \quad (I)$$

wherein $R^1-C^*HX-Q-$ and $-X'-Q'-C^*HY-R^5$ are identical optically active radicals selected from the group $-O-C^*HCH_3-COO-n-$ alkyl, $-O-C^*HCH_3-CH_2-O-n-$alkyl, $-COO-C^*HCH_3-COO-n-$alkyl, $-O-CO-C^*HCH_3-O-n-$alkyl, $-OCH_2-C^*HCH_3-O-n-$alkyl, $-COO-C^*HCH_3-CH_2-O-n-$alkyl, $-OC^*HCH_3-CH_2-COO-n-$alkyl, $-COO-C^*HCH_3-CH_2-COO-n-$alkyl, $-OCH_2-C^*HCH_3-COO-n-$alkyl or $-COO-CH_2-C^*HCH_3-COO-n-$alkyl, alkyl is of 1–12 C atoms, and $-A^4-Z^1-A^2-(Z^2-A^3)_n-$ is a group of the following formulae.

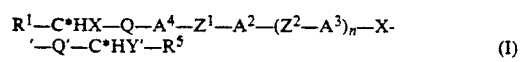

1

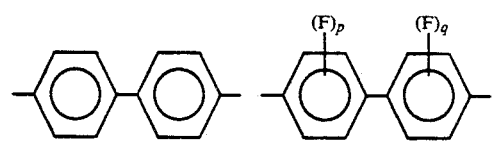

2

(p = 1, 2, 3, or 4;
q = 0, 1, 2, 3 or 4)

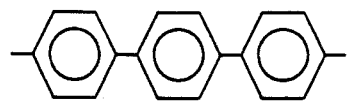

3

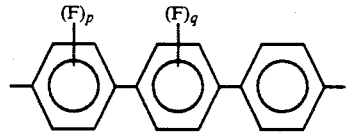

4

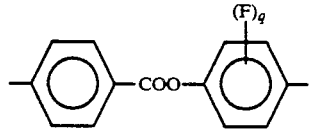

11

2. An optically active compound according to claim 1, of the formula

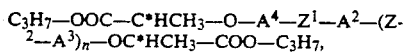

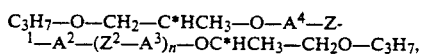

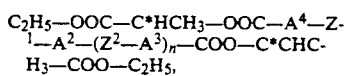

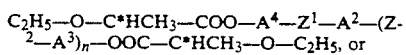

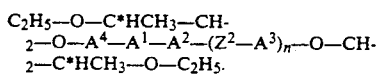

3. An optically active compound according to claim 1, which is 4,4'-bis-(α-pentyloxypropanoyloxy)-biphenyl, 4,4'-bis-(α-butyloxypropanoyloxy)-biphenyl, 4,4'-bis-(α-propyloxypropanoyloxy)-biphenyl, or 4,4'-bis-(α-ethyloxypropanoyloxy)-biphenyl.

4. A chiral tilted smectic liquid crystal phase with at least two liquid crystal components, containing at least one optically active compound of the formula I according to claim 1.

5. Electrooptical display element comprising a liquid crystal dielectric, wherein a phase according to claim 4 is the dielectric.

* * * * *

UNITED STATES PATENT AND TRADEMARK OFFICE
CERTIFICATE OF CORRECTION

PATENT NO. : 5,064,569
DATED : November 12, 1991
INVENTOR(S) : Thomas GEELHAAR et al.

It is certified that error appears in the above-identified patent and that said Letters Patent is hereby corrected as shown below:

The Title Page; -- Item [75]

The forth inventor's name was omitted.  Please add Hans A. Kurmeier, SEEHEIM-JUGENHEFED, GERMANY

Signed and Sealed this

Ninth Day of March, 1993

*Attest:*

STEPHEN G. KUNIN

*Attesting Officer*     Acting Commissioner of Patents and Trademarks